US007340028B2

(12) United States Patent
Grass et al.

(10) Patent No.: US 7,340,028 B2
(45) Date of Patent: Mar. 4, 2008

(54) METHOD AND DEVICE FOR VOLUMETRIC IMAGE RECONSTRUCTION

(75) Inventors: Michael Grass, Buchholz in der Nordheide (DE); Robert Manzke, Husberg (DE); Thomas Köhler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 213 days.

(21) Appl. No.: 10/546,064

(22) PCT Filed: Feb. 10, 2004

(86) PCT No.: PCT/IB2004/000414

§ 371 (c)(1),
(2), (4) Date: Aug. 18, 2005

(87) PCT Pub. No.: WO2004/075115

PCT Pub. Date: Sep. 2, 2004

(65) Prior Publication Data

US 2006/0062346 A1 Mar. 23, 2006

(30) Foreign Application Priority Data

Feb. 19, 2003 (EP) .................................. 03100386

(51) Int. Cl.
*A61B 6/03* (2006.01)
(52) U.S. Cl. ......................................... 378/8; 378/901

(58) Field of Classification Search .................... 378/4, 378/8, 15, 19, 901
See application file for complete search history.

(56) References Cited

U.S. PATENT DOCUMENTS

| 6,104,775 A | 8/2000 | Tuy |
| 6,343,108 B1 | 1/2002 | Heuscher |
| 6,522,712 B1 * | 2/2003 | Yavuz et al. ................... 378/4 |
| 2002/0122529 A1 | 9/2002 | Heuscher |

OTHER PUBLICATIONS

Grass, M., et al.; Helical cardiac cone beam reconstruction using retrospective ECG gating; 2003; Phys. Med. Biol.; 48:3069-3084.
Kachelriess, M., et al.; ECG-correlated image reconstruction from subsecond multi-slice spiral CT scans of the heart; 2000; Med. Phys; 27(8):1881-1902.
Proksa, R., et al.; The n-PI-Method for Helical Cone-Beam CT; 2000; IEEE Trans. on Med. Imag.; 19(9):848-863.

* cited by examiner

*Primary Examiner*—Chih-Cheng G Kao

(57) ABSTRACT

The reconstruction of computer tomography data is very often based on a parallel rebinning step of the projection data prior to the filtered back projection. In case of cardiac reconstruction, a gating technique is applied to select appropriate projections for a time-dependent image reconstruction. Usually, the gating window is a function of the fan-beam/cone-beam projection only. According to the present invention, a function corresponding to the location on the detector surface, where the respective projection was detected is used to further verify whether the respective projection is truly within the selected gating window or not.

20 Claims, 6 Drawing Sheets

FIG. 3 a-f

METHOD AND DEVICE FOR VOLUMETRIC IMAGE RECONSTRUCTION

The present invention relates to the art of image reconstruction. It finds particular application in conjunction with reconstructing x-ray transmission data from computer tomographic (CT) scanners which move a cone-beam or fan-beam of radiation relative to the object of interest, and will be described with particular reference thereto. However, it is to be appreciated that the present invention will also find application in conjunction with the reconstruction of data from CT-scanners, nuclear cameras and other diagnostic scanners that process data representing non-parallel trajectories. In particular, the present invention relates to a method of volumetric image reconstruction to an image processing device for volumetric image reconstruction and to a computer program product comprising a computer readable medium usable for volumetric image reconstruction.

Conventionally, spiral or helical CT-scanners include x-ray source which projects a thin slice or beam of penetrating radiation. The x-ray sources mounted for rotational movement about an object that is translated along the axis of rotation. An arc or ring of radiation detectors receive radiation which has traversed the object. Data from the radiation detectors represents a single spiraling slice through the subject. The data from the detectors is reconstructed into a 3-dimensional image representation.

The reconstruction of CT data is often based on a parallel rebinning step of the projection data prior to a filtered back-projection. This holds true for single line and cone beam projection data, respectively. For the reconstruction of CT data acquired from an object with a movement, such as the human heart, the situation is complicated by the fact that the heart carries out an almost periodic movement. In order to perform a higher resolution reconstruction of a single phase of the heart, gating approaches are applied. The gating window is typically determined from the electrocardiogram (ECG) and restricts the amount of the available projection data to that belonging to the heart phase of interest.

In all cases known up to now, the gating window is used to label the parallel rebinned projections which will be used for the reconstruction.

The parallel rebinning itself generates a parallel projection from a number of fan-beam/cone-beam projections acquired different source positions. Accordingly, the number of fan-beam/cone-beam projections are acquired at different points in time. A parallel rebinned projection contains information from a set of fan-beam/cone-beam projections which have been measured within an angular range of the fan angle. It is only the central ray of the parallel projection of the parallel rebinning which has been measured at the same point in time as the fan-beam projection which has been acquired under the same projection angle. Therefore, the straightforward labeling of parallel rebinned projections with the values resulting from the ECG based gating windows will lead to the use of projection data in the reconstruction which did not belong to the gating window and thereby causes unwanted motion artifacts in the image.

It is an object of the present invention to reduce unwanted motion artifacts in the images.

According to an exemplary embodiment of the present invention, the above object may be solved by a method of volumetric image reconstruction from a plurality of projections of an object, wherein a plurality of projections is determined by means of a source of radiation and a corresponding detector which are moved relative to the object on a scan path such as a helical scan path, wherein the method comprises the steps of performing a rebinning step for the plurality of projections for determining a plurality of rebinned projections and determining whether a respective one of the plurality of rebinned projections is within a gating window on the basis of location information with respect to a location where the respective one of the plurality of rebinned projections was detected on the detector. Advantageously, according to this exemplary embodiment of the present invention, unwanted motion artifacts in an image after the volumetric image reconstruction are reduced. Thus, the resolution, for example when a high temporal resolution cardiac CT reconstruction is performed, can be improved.

According to another exemplary embodiment a function depending on the location on the detector where the respective one of the plurality of rebinned projections was detected is determined, wherein the function transfers the labeling of the plurality of projections into a rebinned projection space of the plurality of rebinned projections. This function is used to verify whether a voxel corresponding to the respective one of the plurality of rebinned projections truly is within the gating window or not. Advantageously, this exemplary embodiment of the present invention allows for a verified and dependable determination of whether the voxel is within the gating window and should be used for reconstruction of the final image or not.

According to another exemplary embodiment a weighting, a filtering and a normalization of the weighting is carried out to determine whether the voxel is projected onto an allowable area in the rebinned projection space.

According to another exemplary embodiment the plurality of projections are determined by means of a CT-scanner and the method is for a high temporal resolution CT reconstruction where the gating window is determined from a electrocardiogram. Alternatively, an acoustic sensor or an optical sensor may be used instead of the ECG.

According to another exemplary the rebinning step comprises a parallel rebinning and the movement of the source of radiation and the detector is along a helical path.

According to another exemplary embodiment there is provided an image processing device with a calculation unit wherein the calculation unit is constructed to perform a rebinning for a plurality of projections for determining a plurality of rebinned projections and wherein the calculation unit is further constructed to determine whether a respective one of the plurality of rebinned projections is within the gating window on the basis of location information with respect to a location where the respective one of the plurality of rebinned projections was detected on a detector.

Further exemplary embodiments of the image processing device are provided.

According to another exemplary embodiment there is provided a computer program product comprising a computer readable medium with a computer program means to make a computer execute a rebinning step and a determination whether a respective one of a plurality of rebinned projections is within a gating window on the basis of location information when the computer program is executed on the computer. Advantageously, the computer program according to this exemplary embodiment requires a minimal amount of calculations to be performed and thereby reduces an amount of required calculation power. Also, a storage necessary to execute the computer program can be minimized.

It may be seen as the gist of an exemplary embodiment of the present invention that a location information corresponding to a location on the detector where a certain projection was detected, is used to decide whether this projection truly lies within the gating window.

These and other aspects of the present invention will become apparent from and elucidated with reference to the embodiments described hereinafter.

Exemplary embodiments of the present invention will be described in the following, with reference to the following drawings.

Figure 6:
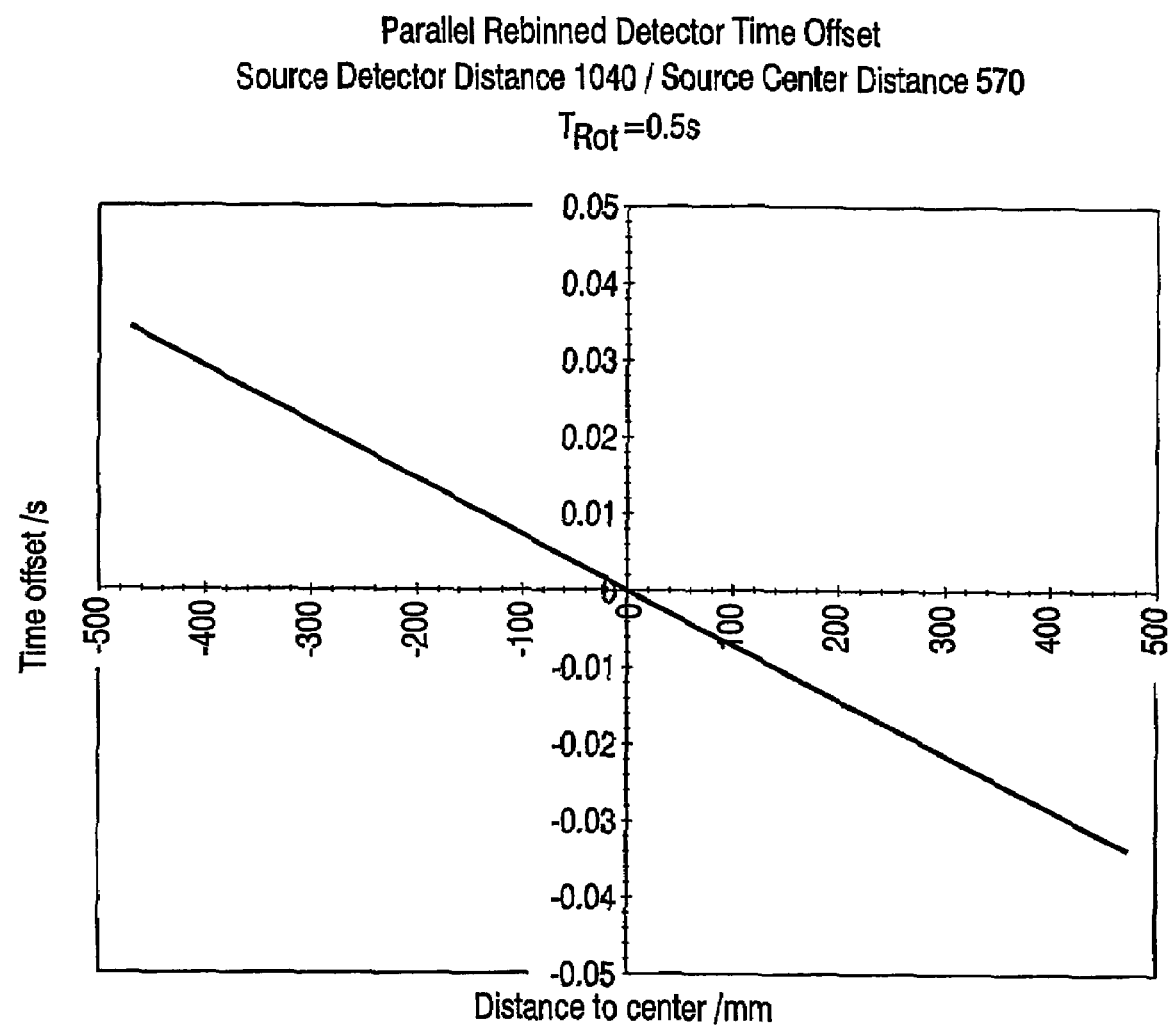

FIG. 6 describes time values as a function of a distance from the center of rotation of the source of radiation and the detector for a parallel rebinned detector for a CT-system with 0.5 seconds rotation time.

In the following description, the present invention is explained along an exemplary embodiment of a parallel rebinning. However, the present invention may be applied to each type of rebinning where new artificial projections are reconstructed from a plurality of other projections which have been taken in another geometry at other moments in time. In other words, the present invention may be applied to any suitable scan-trajectory where a rebinning is performed into another projection geometry.

Figure 1:
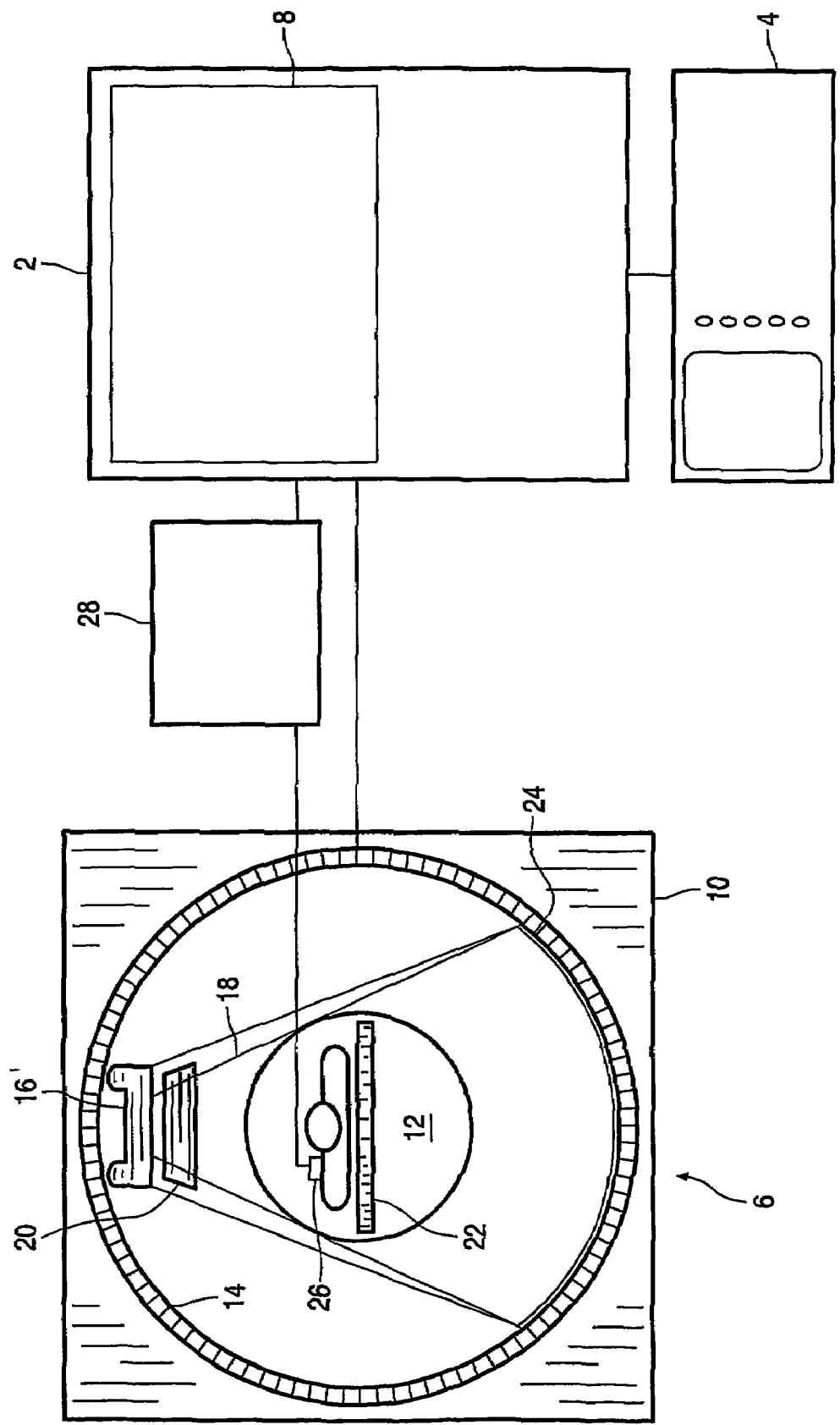
FIG. 1 shows and exemplary embodiment of an image processing device connected to a CT-scanner according to the present invention.

FIG. 1 shows a schematic simplified representation of an image processing device 2 connected to an input/output unit 4 and to a CT-scanner 6 according to an exemplary embodiment of the present invention. The image processing device 2 comprises a calculation unit 8. The computer tomographic CT-scanner 6 comprises a stationary gantry 10 which defines an examination region 12. Reference character 14 designates a rotating gantry, which is mounted to the stationary gantry 10. A source of penetrating radiation 16 such as an x-ray tube is arranged on the rotating gantry 14 for rotation therewith. The radiation source 16 is collimated to produce a cone-shaped beam of radiation 18, which passes through the examination region 12 during rotation of the rotating gantry 14.

Furthermore, there is provided a collimator and shutter system 20 for shaping the beam of radiation 18 and for selectively gating the beam 18 on and off. Also, the radiation beam 18 may be gated on and off by means of electronically switching the source of radiation 16.

Reference character 22 designates an object support such as a patient couch, supporting the object to be scanned such that a region of interest of the object is at least partially within the examination region 12 of the CT-scanner 6. On the rotating gantry 14, on a position opposite to the source of radiation 16, there is provided a radiation detector 24. The radiation detector 24 is arranged such that it detects a substantial amount of the cone beam 18 emitted by the radiation source 16 after passing through the object in the examination region 12. Preferably, the radiation detector is a 2-dimensional detector array. Furthermore, the radiation detector 24 is mounted to the rotating gantry 14 for rotation therewith such that the radiation detector 24 rotates together with the radiation source 16 around the examination region 12.

During rotation of the rotating gantry 14 around the examination region 12, the object support 22 holding the object of interest thereon is translated along a central horizontal axis of the examination region 12. Due to this, the radiation source 16 and the radiation detector 24 follow a helical path relative to the object of interest. Optionally, in an alternative embodiment, the support 22 may remain stationary while the stationary gantry 10 is arranged such that it is translated or otherwise moved relative to the object of interest such that the source of radiation 16 and the radiation detector 24 are displaced along the helical path relative to the object of interest during a scan.

During a scan, the radiation detector 24 is sampled at predetermined time intervals. The sampling results read from the radiation detection 24 are electrical signals, i.e. electrical data, which is referred to as projection in the following. A whole data set of a whole scan of an object of interest therefore consists of a plurality of projections where the number of the projections corresponds to the time interval with which the radiation detector 24 is sampled. The plurality of projections are transmitted to the image processing device 2 where they are read by means of a calculation unit 8. On the basis of the plurality of projections, the calculation unit 8 reconstructs slice images of the object of interest along a plane perpendicular to the central horizontal axis of the examination region 12. Instead of generating slice images, the calculation unit 8 may also be constructed to determine 3-dimensional images or animated representations where for example individual images are put together such that an animated sequence of images showing for example the periodic movement of the human heart is generated. The images can be out-put via the input/output unit 4. Furthermore, the input/output unit 4 allows an operator to manually control parameters of the scan in the CT-scanner 6 and the image processing device 2. In an alternative embodiment, an aperture system such as a diaphragm may be provided between the radiation source 16 and the examining region 12 such that instead of the cone beam 18, a fan beam is generated.

Reference character 26 in FIG. 1 designates a sensor attached to the thorax of a patient to be examined. The sensor 26 is connected to an electrocardiogram (ECG) 28 which is connected to the image processing device 2. Alternatively, instead of the ECG, the gating function may also be determined directly from the projections (Kymogram), or by means of other sensors such an acoustic sensor or an optical sensor.

The present invention will be further described with reference to the example of a high temporal resolution cardiac CT reconstruction where a high resolution reconstruction of a single phase of the heart is made. However, it has to be noted that the present invention is not limited to the high temporal resolution cardiac CT reconstruction but can be generally applied in conjunction with the reconstruction of data from CT scanners, nuclear cameras and other diagnostic scanners where an object having a movement, such as a periodic movement, is examined.

Figure 2:
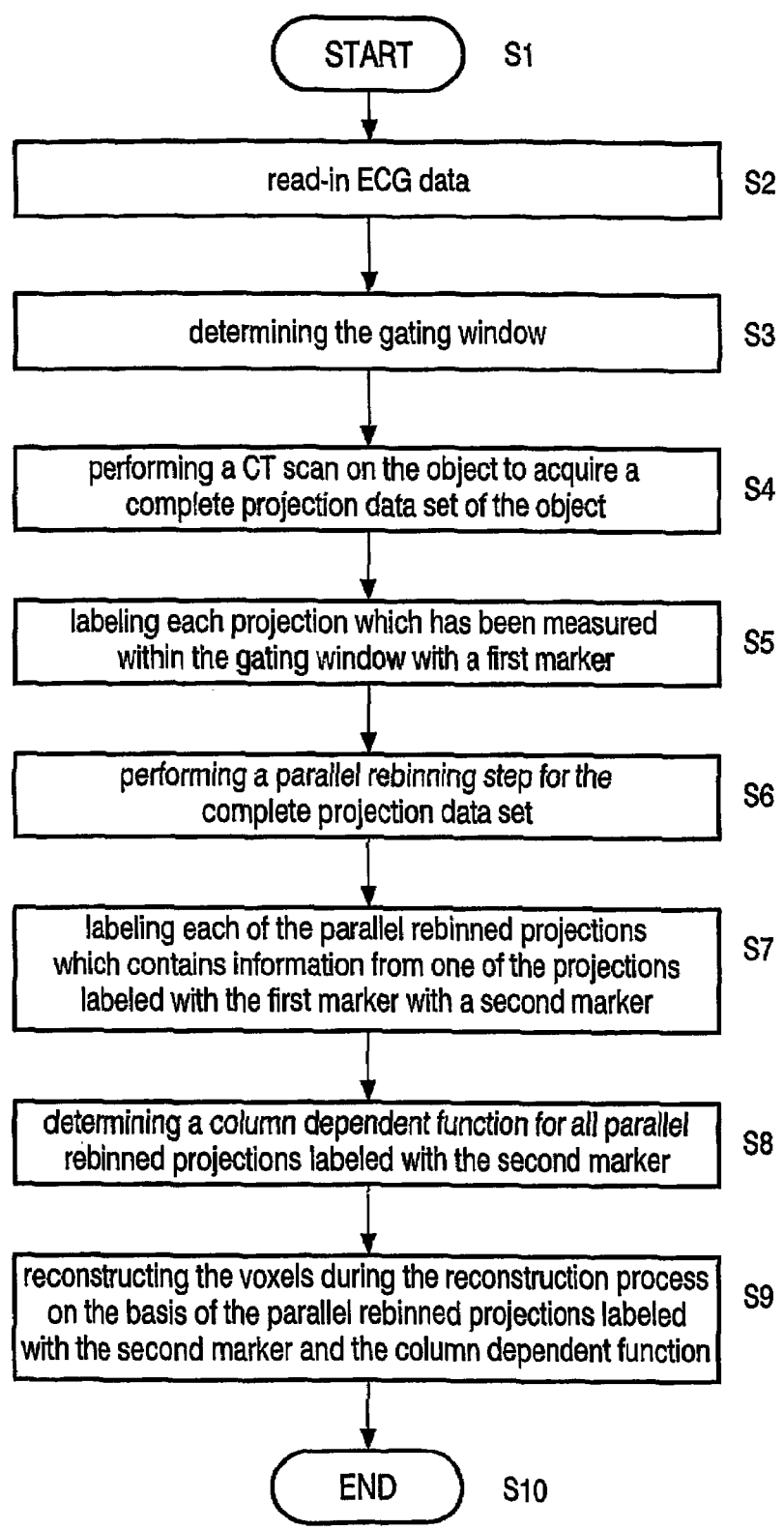
FIG. 2 is a flow-chart of an exemplary embodiment of a method for operating the device of FIG. 1.

In the following, an exemplary embodiment of an operation of the system shown in FIG. 1 will be described with reference to FIG. 2. FIG. 2 shows a simplified flow-chart of an exemplary embodiment of a method according to the present invention for operation the system of FIG. 1.

After the start in step S1 where, for example, an operator initiates the operation of the system of FIG. 1 via the input into the input/output unit 4, ECG data is read in from the ECG 28 in step S2. The ECG data represents the heart beat of the patient measured by means of the sensor 26.

Then, the method continues to step S3 where, based on the measured ECG data read into the image processing device 2, i.e. the calculation unit 8 of the image processing device 2, the calculation unit 8 determines a gating window width and position within a R-R interval of the ECG. This can be done with the interaction of an operator such as a cardiologist. The R-R interval is the interval between beat annotations of the human heart. This window width and position may be constant or varying over the total acquisition interval. The total acquisition interval is defined as ranging from the first projection to the last projection, including all or some of the protections determined during the scan at the CT-scanner.

After the determination of the gating window in step S3, the method continues to step S4, where the image processing device 2 controls the CT-scanner 6 such that a CT-scan is performed on the patient to acquire a complete projection data set of the patient.

Instead of subsequently reading the ECG data and the CT projections, advantageously, the ECG data and the CT projections are determined in parallel. Two gating methods may be applied: a retrospective gating and a prospective gating.

In the retrospective gating, the projections and the ECG data are continuously determined and then, i.e. from hindsight, a determination is made from the ECG data with respect to the location of the gating window and with respect to which of the projections are to be used for the reconstruction of the image.

In the prospective gating, ECG data and the CT projections are again determined in parallel. However, at the beginning of each cycle of the heart (R-peak), a decision is made in which part of the cycle the projections are to be determined. Then, the acquisition interval may be controlled such that the tube (radiation source) is only switched on for this short interval of the cycle and projections are only determined during this interval.

After the scan in step S4, the method continues to step S5, where the calculation unit 8 in the image processing device 2 labels each projection which has been measured within the gating window defined in step S3 with a first marker. In other words, in step S5, each of the acquired projections (cone beam or fan beam) is labeled with the first marker, if it has been measured within the gating window of one of the cardiac cycles during which the scan took place.

Figure 3:
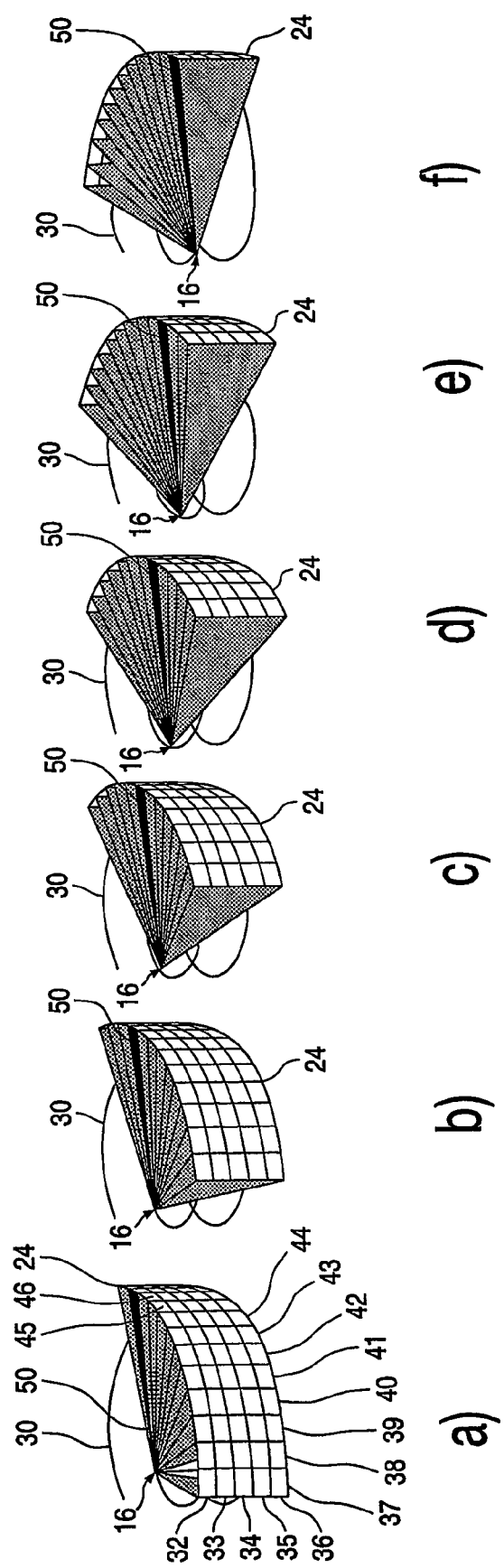
FIGS. 3a to 3f are simplified representations for further explaining the method of FIG. 2.

After the labeling step S5, the calculation unit 8 performs a rebinning step. In step S6, the calculation unit 8 performs a parallel rebinning for a complete projection data set. This will be described in further detail with reference to FIG. 3a to FIG. 4.

As already indicated with reference to FIG. 1, the radiation source 16 and the radiation detector 24 rotate together around the patient. In FIGS. 3a to 3f, reference character 30 designates the helical path along which the radiation source 16 and the radiation detector 24 are rotated. This is illustrated in FIGS. 3a to 3f, where subsequent projections are shown along the helical path of the radiation source 16 and the radiation detector 24. In FIGS. 3a to 3f, the radiation detector 24 is depicted as a two-dimensional detector array having a plurality of lines 32 to 36 and a plurality of columns 37 to 46.

During the parallel rebinning step S6, parallel projections, i.e. parallel rays or columns of a plurality of projections are used for reconstructing the final image. These parallel projections are designated with the reference character 50. In the detector arrangement shown in FIGS. 3a to 3f, each of the parallel projections 50 selected during the rebinning step corresponds to a column 37 to 44 of the two-dimensional detector array 24. As may be taken from FIGS. 3a to 3f, the parallel projections 50 have a plane parallel to each other.

However, as also may be taken from FIGS. 3a to 3f, each of the parallel projections 50 impinges onto the two-dimensional detector array 24 at a different location. In other words, in the detector arrangement 24 depicted in FIGS. 3a to 3f, each of the parallel projections 50 selected during the rebinning is detected by means of a different column 37 to 44 of the two-dimensional detector array 24.

Figure 4:
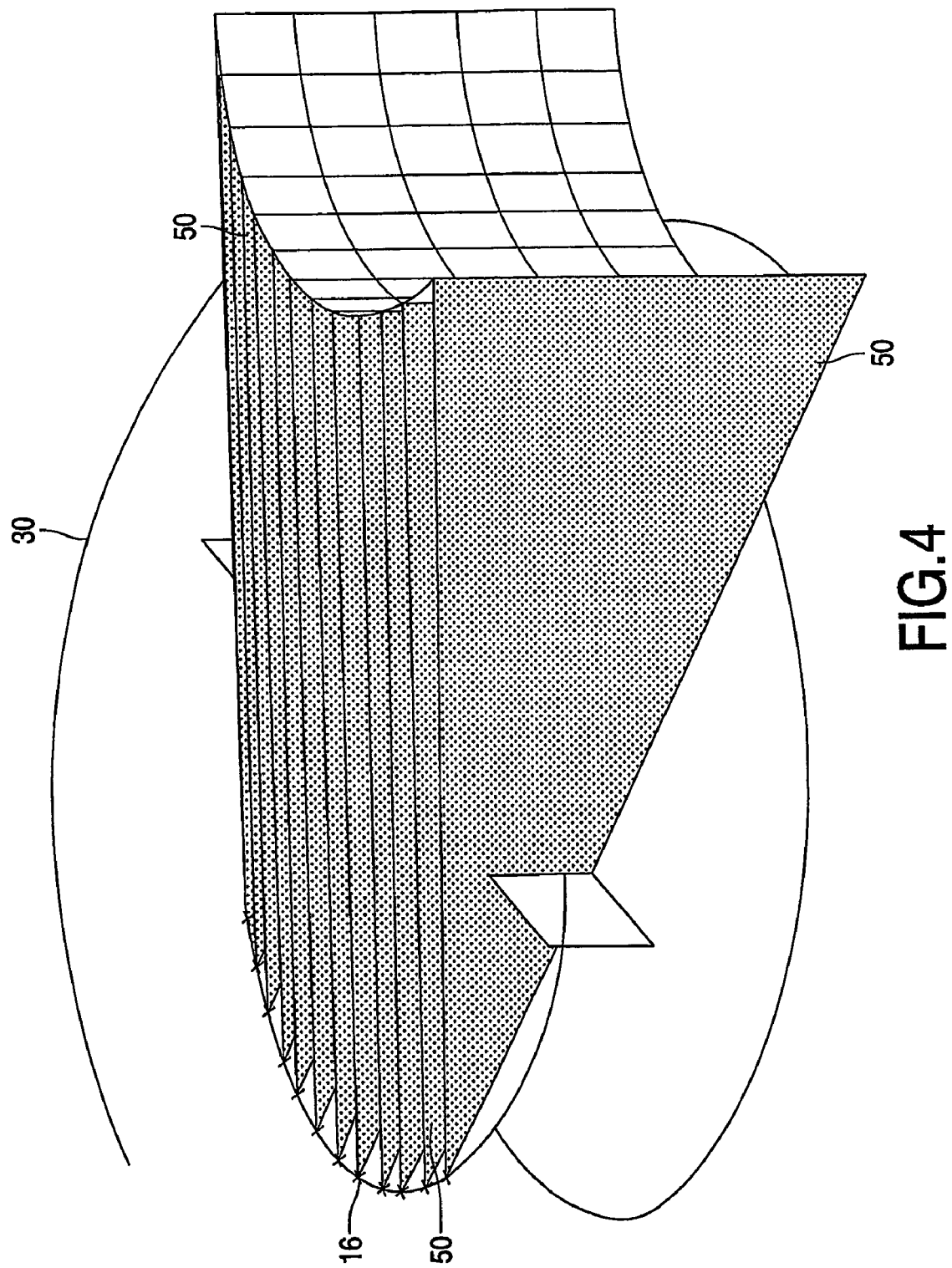
FIG. 4 is a simplified graphical representation of a rebinning process for further explaining the method of FIG. 2.

In the following, a further part of the rebinning step will be described with reference to FIG. 4. As shown in FIG. 4, a plurality of parallel projections 50 are put together to a data set consisting of a plurality of parallel projections 50. This data set is referred to in the following as parallel rebinned projections.

In the following step S7, each of the parallel rebinned projections which contains information from one of the projections labeled with the first marker is labeled with a second marker. Then, in the following step S8, a column-dependent function is determined for all parallel rebinned projections labeled with the second marker. In other words, with reference to FIGS. 3a to 3f, a function is determined depending on which of the columns 37 to 44 of the detector array 24 detected the respective parallel projection 50. Thus, according to the present invention, on the basis of a location information relating to the position of the radiation detector 24 where the respective parallel ray 50 was detected, the column-dependent function is determined for all parallel rebinned projections containing information from the projections labeled with the first marker.

In the following step S9, on the basis of the parallel rebinned projections labeled with the second marker and the column-dependent function, during the reconstruction process, the voxels for the subsequent image representation are reconstructed. After the reconstruction of the voxels in step S9, the method continues to step S10, where it ends. In other words, according to the present invention, the gating window that is originally a function of the fan-beam/cone-beam projection only, becomes a function of the protection angle and the column-coordinate of the radiation detector 24 after parallel rebinning. Advantageously, by incorporating such location information on the column-coordinate of the radiation detector 24 during back projection, the temporal resolution of the reconstruction method can be increased significantly, since only data is used for reconstructing the image from parallel projections 50 that truly belong to the chosen gating window.

Figure 5:
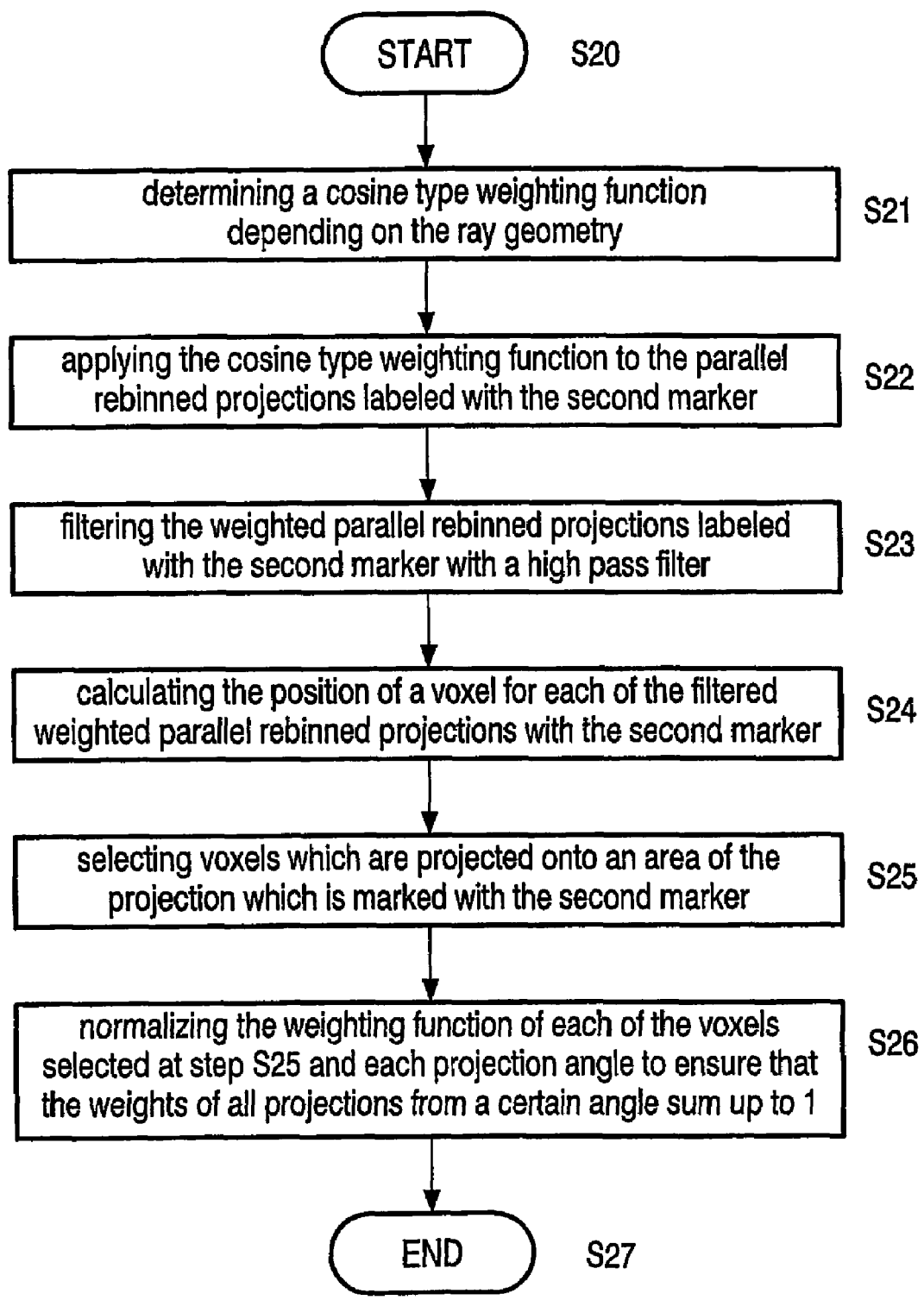
FIG. 5 is a flow-chart of an exemplary embodiment of step S9 of the method of FIG. 2 according to the present invention.

In the following, an exemplary embodiment of step S9 of FIG. 2 will be described with reference to FIG. 5. FIG. 5 shows a flow-chart of an exemplary embodiment of step S9 of FIG. 2. After the start in step S20, a cosine type weighting function depending on the ray geometry of the CT-scanner 6 is determined in step S21. The ray geometry includes information on at least one element selected from the group consisting of the helical path, the dimensions of the cone-beam or the fan-beam, the position of the radiation detector 24 with respect to the radiation source 16 and location information with respect to the lines and columns of the radiation detector 24. Then, after step S22, the cosine type weighting function is applied to the parallel rebinned projections labeled with the second marker in step S22. After the labeling in step S22, the method continues to step S23, where the weighted parallel rebinned projections labeled with the second marker are filtered by means of a suitable high pass filter. Then, after the filtering in step S23, a position of a voxel for each of the filtered weighted parallel rebinned projections with the second marker is calculated in step S24. Then, the method continues to step S25.

In step S25, voxels are selected which are projected onto an area of the projection which is marked with the second marker. In other words, in step S27, a test is made whether the determined voxel truly is within the gating window. For this, the voxel is "projected" onto the detector 24 and a determination is made whether the voxel is projected into a gating window area on the detector 24. As described above, the gating window area corresponds to a "projection area" of the gating window onto the surface of the radiation detector 24.

After step S25, the method continues to step S26, where a normalization step is carried out. In step S26, the weighting function of each of the voxels selected at step S25 and each projection are normalized to ensure that the sum weight of all projections from a certain angle amounts to one. After the normalization in step S26, the method continues to step S27, where it ends.

FIG. 6 shows time values as a function of a distance from a center of rotation of the rotating gantry 14 for a parallel rebinned detector for a CT-system with 0.5 seconds rotation time. For a real detector system a variation of 68 milliseconds over the range of a projection can be seen. For a circle with 288 mm round the center of rotation, a variation of 20 milli-seconds remains.

As described above, the parallel rebinning itself generates a parallel projection from a number of fan-beam or cone-beam projections acquired at different source positions on the helical path 30 and therefore, at different points in time. The parallel rebinned projection contains information from a set of fan-beam or cone-beam projections which have been measured within an angular range of the fan angle. However, it has to be noted that it is only the central ray of the parallel projection which has been measured at the same point in time as the fan-beam projection, which has been applied under the same projection angle. Therefore, the straightforward labeling of parallel rebinned projections within the values resulting from the ECG based gating window leads to the use of projection data in the reconstruction which did not truly belong to the gating window and thereby causes unwanted motion artifacts or defects in the image. According to the present invention, such unwanted motion artifacts or defects can be significantly reduced since, according to the present invention a test is made whether the projection data finally used for the reconstruction of the final image lies within the gating window or not by using location information. The information with respect to at which location of the detector 24 the respective protection data was detected is used to further check whether the projection data used for final reconstruction of the image lies within the gating window or not.

As already indicated above, apart from being used in the high temporal resolution cardiac CT reconstruction, the present invention may also be applied to applications in conjunction with nuclear cameras and other diagnostic scanners where a moving object is to be scanned.

The invention claimed is:

1. A method of volumetric image reconstruction from a plurality of projections of an object, wherein a plurality of projections is determined by means of a source of radiation and a corresponding detector which are moved relative to the object, the method comprising the steps of:
performing a rebinning step for the plurality of projections for determining a plurality of rebinned projections;
determining whether a respective one of the plurality of rebinned projections is within a gating window on the basis of location information with respect to a location where the respective one of the plurality of rebinned projections was detected on the detector.

2. The method of claim 1, further comprising the steps of:
defining a gating window;
labelling each of the plurality of projections which has been detected within a gating window with a first marker;
labelling each of the plurality of rebinned projections which contains information of one of the plurality of projections labelled with the first marker with a second marker;
wherein the step of determining whether a respective one of the plurality of rebinned projections is within a gating window on the basis of location information with respect to a location where the respective one of the plurality of rebinned projections was detected on the detector further comprises the steps of:
determining the location information with respect to a location where the respective one of the plurality of rebinned projections labelled with the second marker was detected on the detector;
determining a function depending on the location on the detector where the respective one of the plurality of rebinned projections labelled with the second marker was detected, wherein the function transfers the labelling of the plurality of projections into a rebinned projection space of the plurality of rebinned projections;
determining a voxel corresponding to the respective one of the plurality of rebinned projections labelled with the second marker; and
verifying whether the voxel corresponding to the respective one of the plurality of rebinned projections labelled with the second marker is within the gating window on the basis of the function.

3. The method of claim 2, further comprising the steps of:
determining a weighting function depending on a ray geometry of a radiation emitted by the source of radiation;
applying the weighting function to the plurality of rebinned projections labelled with the second marker;
filtering the plurality of weighted rebinned projections labelled with the second marker;
calculating a position of the voxel for the respective one of the plurality of filtered weighted rebinned projections labelled with the second marker in the rebinned projection space;
determining whether the voxel is projected onto an allowable area in the rebinned projection space on the basis of the function; and
normalizing the weighting function for the voxel to ensure that weights of all projections from a certain angle sum up to one;
back projecting the allowed detector values multiplied with the weighting function to the voxel.

4. The method of claim 1, wherein the method is for a high temporal resolution CT reconstruction; wherein the plurality of projections are determined by means of a CT-scanner; and wherein the gating window is determined from an electrocardiogram.

5. The method of claim 1, wherein the rebinning step comprises a parallel rebinning and wherein the movement of the source of radiation and the detector is along a helical path.

6. The method of claim 1, further including:
determining a width and a position of the gating window within an interval between heart cycles recorded with an electrocardiograph.

7. The method of claim 1, wherein the detector includes an array of radiation sensitive sensors having a plurality of columns of radiation sensitive sensors and the location information for each of the plurality of rebinned projections indicates the column at which the detector detected the corresponding rebinned projection.

8. The method of claim 7, further including:
prior to rebinning the plurality of projections, labelling the projections corresponding to the gating window with a first marker.

9. The method of claim 8, further including:
labelling the rebinned projections that include the first marker with a second marker.

10. The method of claim 9, further including:
determining a detector column-dependent function for the parallel rebinned projections labeled with the second marker.

11. The method of claim 10, wherein the gating window is a function of the detector column-dependent function.

12. The method of claim 11, further including:
weighting the plurality of rebinned projections labelled with the second marker;
filtering the plurality of weighted rebinned projections; and
determining a position of a voxel for each filtered rebinned projection.

13. The method of claim 12, further including:
determining whether the voxels correspond to the gating window.

14. The method of claim 13, further including:
normalizing the weighted rebinned projections that correspond to the gating window.

15. The method of claim 14, further including:
reconstructing the normalized projections to generate volumetric image data.

16. An image processing device for volumetric image reconstruction from a plurality of projections of an object, wherein a plurality of projections is determined by means of a source of radiation and a corresponding detector which are moved relative to the object, the image processing device comprising a calculation unit;
wherein the calculation unit is constructed to perform a rebinning for the plurality of projections for determining a plurality of rebinned projections; and
wherein the calculation unit is further constructed to determine whether a respective one of the plurality of rebinned projections is within a gating window on the basis of location information with respect to a location where the respective one of the plurality of rebinned projections was detected on the detector.

17. The image processing device of claim 16, wherein the calculation unit is further constructed to determine a gating window;
wherein the calculation unit is further constructed to label each of the plurality of projections which has been detected within a gating window with a first marker;
wherein the calculation unit is further constructed to label each of the plurality of rebinned projections which contains information of one of the plurality of projections labelled with the first marker with a second marker;
wherein the calculation unit is further constructed to determine the location information with respect to a location where the respective one of the plurality of rebinned projections labelled with the second marker was detected on the detector;
wherein the calculation unit is further constructed to determine a function depending on the location on the detector where the respective one of the plurality of rebinned projections labelled with the second marker was detected,
wherein the function transfers the labelling of the plurality of projections into a rebinned projection space of the plurality of rebinned projections;
wherein the calculation unit is further constructed to determine a voxel corresponding to the respective one of the plurality of rebinned projections labelled with the second marker; and
wherein the calculation unit is further constructed to verify whether the voxel corresponding to the respective one of the plurality of rebinned projections labelled with the second marker is within the gating window on the basis of the function.

18. The image processing device of claim 17, wherein the calculation unit is further constructed to determine a weighting function depending on a ray geometry of a radiation emitted by the source of radiation;
wherein the calculation unit is further constructed to apply the weighting function to the plurality of rebinned projections labelled with the second marker;
wherein the calculation unit is further constructed to filter the plurality of weighted rebinned projections labelled with the second marker;
wherein the calculation unit is further constructed to calculate a position of the voxel for the respective one of the plurality of filtered weighted rebinned projections labelled with the second marker in the rebinned projection space;
wherein the calculation unit is further constructed to determine whether the voxel is projected onto an allowable area in the rebinned projection space on the basis of the function; and
wherein the calculation unit is further constructed to normalize the weighting function for the voxel to ensure that weights of all projections from a certain angle sum up to one.

19. The image processing device of claim 16, wherein the image processing device is a part of a computer tomograph; wherein the gating window is determined from an electrocardiogram.

20. A computer program product comprising a computer readable medium, having thereon: computer program means to make a computer execute the following steps when the computer program is executed on the computer:
performing a rebinning step for the plurality of projections for determining a plurality of rebinned projections;
determining whether a respective one of the plurality of rebinned projections is within a gating window on the basis of location information with respect to a location where the respective one of the plurality of rebinned projections was detected on the detector.

* * * * *